United States Patent
Muldoon

(10) Patent No.: US 10,746,666 B2
(45) Date of Patent: *Aug. 18, 2020

(54) NON-INVASIVE WINE TAINT DETECTOR

(71) Applicant: Cecilia Muldoon, Oxford (GB)

(72) Inventor: Cecilia Muldoon, Oxford (GB)

(73) Assignee: VeriVin Ltd., Long Hanborough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/140,698

(22) Filed: Sep. 25, 2018

(65) Prior Publication Data
US 2019/0025228 A1  Jan. 24, 2019

Related U.S. Application Data

(63) Continuation of application No. 15/246,722, filed on Aug. 25, 2016, now Pat. No. 10,107,764, which is a
(Continued)

(51) Int. Cl.
 G01N 21/90 (2006.01)
 G01N 33/14 (2006.01)
 (Continued)

(52) U.S. Cl.
 CPC ......... *G01N 21/90* (2013.01); *G01N 15/1429* (2013.01); *G01N 21/3577* (2013.01);
 (Continued)

(58) Field of Classification Search
 CPC ....... G01N 15/1429; G01N 2015/1488; G01N 21/3577; G01N 21/51; G01N 21/65;
 (Continued)

(56) References Cited

U.S. PATENT DOCUMENTS

| 4,830,192 A | * | 5/1989 | Plester | ................. B07C 5/3408 |
| | | | | 209/3.1 |
| 5,444,539 A | * | 8/1995 | van der Grift | ......... B65D 23/14 |
| | | | | 215/12.2 |

(Continued)

FOREIGN PATENT DOCUMENTS

| WO | WO 1988/00862 | 2/1988 |
| WO | WO 2002/33404 | 4/2002 |
| WO | 2016/070094 | 5/2016 |

OTHER PUBLICATIONS

International Search Report and Written Opinion, PCT/US15/588398, dated Feb. 2, 2016, 10 pages.
(Continued)

Primary Examiner — Tri T Ton
(74) Attorney, Agent, or Firm — Fish & Richardson P.C.

(57) ABSTRACT

A system includes a computing device including a memory configured to store instructions. The computing device also includes a processor to execute the instructions to perform operations including initiating transmission of incident light from one or more light sources to a sealed bottle containing liquid. The operations also include receiving scattered light from the liquid contained in the sealed bottle. The operations also include processing one or more signals representative of the scattered light to detect interactions of the incident light with a particular molecule.

20 Claims, 4 Drawing Sheets

Related U.S. Application Data continuation of application No. 14/928,557, filed on Oct. 30, 2015, now Pat. No. 9,453,826.

(60) Provisional application No. 62/073,235, filed on Oct. 31, 2014.

(51) Int. Cl.

| | | |
|---|---|---|
| *G01N 21/3577* | (2014.01) | |
| *G01N 21/65* | (2006.01) | |
| *G01N 15/14* | (2006.01) | |
| *G01N 21/51* | (2006.01) | |
| *G01N 21/88* | (2006.01) | |

(52) U.S. Cl.
CPC .............. *G01N 21/51* (2013.01); *G01N 21/65* (2013.01); *G01N 21/8851* (2013.01); *G01N 33/146* (2013.01); *G01N 2015/1488* (2013.01); *G01N 2201/06113* (2013.01)

(58) Field of Classification Search
CPC ............... G01N 21/8851; G01N 21/90; G01N 2201/06113; G01N 33/146; G01N 30/02; G01N 21/53; G01N 21/9027; G01N 21/49; G01N 33/4905; G01N 33/86; G01N 15/0205; G01N 2015/0288; G01N 2015/0294; G01N 2015/1493; G01N 2030/324; G01N 2030/625; G01N 2033/0081; G01N 21/253; G01N 21/532; G01N 30/16; G01N 30/24; G01N 30/30; G01N 30/461; G01N 30/466; G01N 30/54; G01N 30/60; G01N 30/6052; G01N 30/88; G01N 33/44; G01N 33/442; G01N 35/085; G01N 35/1097; G01N 15/042; G01N 15/1459; G01N 15/1463; G01N 2015/1486; G01N 2021/8822; G01N 21/8803; G01N 2015/1075; G01N 2015/149; G01N 2021/054; G01N 2035/1025; G01N 21/276; G01N 21/4785; G01N 21/9018; G01N 21/9081; G01N 2201/0642; G01N 2201/12723; G01N 33/5005; G01N 33/54326; G01N 33/54373; G01N 33/56966; G01N 33/585; G01N 35/0098; B01D 15/34; B01D 15/08; B01D 15/26; B01D 15/265; G01F 1/74; B01J 19/0046; B01J 19/26; B01J 2219/00274; B01J 2219/00315; B01J 2219/00585; B01J 2219/00587; B01J 2219/00707; B01J 2219/00722; B65D 23/14
USPC ......... 356/337–343, 426–428, 441–442, 432
See application file for complete search history.

(56) References Cited

U.S. PATENT DOCUMENTS

| | | | |
|---|---|---|---|
| 5,510,620 A * | 4/1996 | Achter | ................... G01N 21/51 |
| | | | 250/339.12 |
| 5,750,998 A | 5/1998 | Goldman | |
| 9,453,826 B2 * | 9/2016 | Muldoon | ............. G01N 33/146 |
| 10,107,764 B2 | 10/2018 | Muldoon | |
| 2009/0321646 A1 | 12/2009 | Cozzolino | |
| 2016/0123876 A1 | 5/2016 | Muldoon | |

OTHER PUBLICATIONS

European Search Report for App. Serial No. 15854731.5, dated May 29, 2018.
Gallego et al., "Rapid Measurement of Phenolics Compounds in Red Wine Using Raman Spectroscopy," *IEEE Transactions on Instrumentation and Measurement*, IEEE Service Center, Piscataway, NJ, US, Feb. 2011;60(2):507-512.
Pelletier, "Quantitative Analysis Using Raman Spectrometry," *Appl Spectrosc.*, Jan. 2003;57(1):20A-42A.
Prescott et al., "Estimating a 'Consumer Rejection' Threshold for Cork Taint in White Wine," *Food Quality and Preference*, Longman Scientific and Technical, Harlow GB, Jun. 2005;16(4):345-349.
United Kingdom Office Action for Application No. GB1708586.1, dated Feb. 11, 2020, 7 pages.
Australian Office Action for App. No. 2015338933, dated Mar. 26, 2020, 3 pages.

* cited by examiner

NON-INVASIVE WINE TAINT DETECTOR

CLAIM OF PRIORITY

This application is a continuation application and claims priority under 35 USC § 120 to U.S. patent application Ser. No. 15/246,722, filed Aug. 25, 2016, which is a continuation application of U.S. patent application Ser. No. 14/928,557, filed Oct. 30, 2015 (now U.S. Pat. No. 9,453,826), which claims priority under 35 USC § 119(e) to U.S. Provisional Patent Application Ser. No. 62/073,235, filed on Oct. 31, 2014, the entire contents of which are hereby incorporated by reference.

TECHNICAL FIELD

The description relates generally to a non-invasive system for detecting the contamination of liquids in sealed containers.

BACKGROUND

The last 20 years have seen growing interest and investment in wine worldwide. With this has come a growing expectation of quality. Unfortunately, like other products, wine can fall victim to external influences that render it defective, e.g., poor production practices, inappropriate storage conditions, etc. These not only reduce its quality, but may even render the wine unpalatable or at the very worst undrinkable.

SUMMARY

In one aspect, a computing device implemented method includes initiating transmission of incident light from one or more light sources to a sealed bottle containing liquid. The method also includes receiving scattered light from the liquid contained in the sealed bottle. The method also includes processing one or more signals representative of the scattered light to detect interactions of the incident light with a particular molecule.

Implementations can include one or more of the following features.

In some implementations, the method also includes filtering the scattered light prior to processing one or more signals representative of the scattered light.

In some implementations, processing one or more signals representative of the scattered light includes filtering signals.

In some implementations, filtering the scattered light includes passing frequencies of the received scattered light that are within a particular frequency range.

In some implementations, the method also includes spectrally separating the scattered light prior to processing one or more signals representative of the scattered light.

In some implementations, the liquid is wine.

In some implementations, the particular molecule is trichloroanisole.

In some implementations, processing includes determining from the interactions of the incident light with the trichloroanisole molecule if the wine is tainted.

In some implementations, the light source includes a laser.

In another aspect, a system includes a computing device including a memory configured to store instructions. The computing device also includes a processor to execute the instructions to perform operations including initiating transmission of incident light from one or more light sources to a sealed bottle containing liquid. The operations also include receiving scattered light from the liquid contained in the sealed bottle. The operations also include processing one or more signals representative of the scattered light to detect interactions of the incident light with a particular molecule.

Implementations can include one or more of the following features.

In some implementations, the liquid is wine.

In some implementations, the particular molecule is trichloroanisole.

In some implementations, processing includes determining from the interactions of the incident light with the trichloroanisole molecule if the wine is tainted.

In some implementations, the light source includes a laser.

In another aspect, one or more computer-readable media store instructions that are executable by a processing device. Upon such execution, the instructions cause the processing device to perform operations including initiating transmission of incident light from one or more light sources to a sealed bottle containing liquid. The operations also include receiving scattered light from the liquid contained in the sealed bottle. The operations also include processing one or more signals representative of the scattered light to detect interactions of the incident light with a particular molecule.

In some implementations, the liquid is wine.

In some implementations, the particular molecule is trichloroanisole.

In some implementations, processing includes determining from the interactions of the incident light with the trichloroanisole molecule if the wine is tainted.

In some implementations, the light source includes a laser.

These and other aspects, features, and various combinations may be expressed as methods, apparatus, systems, means for performing functions, program products, etc.

Other features and advantages will be apparent from the description and the claims.

DETAILED DESCRIPTION

Figure 1:
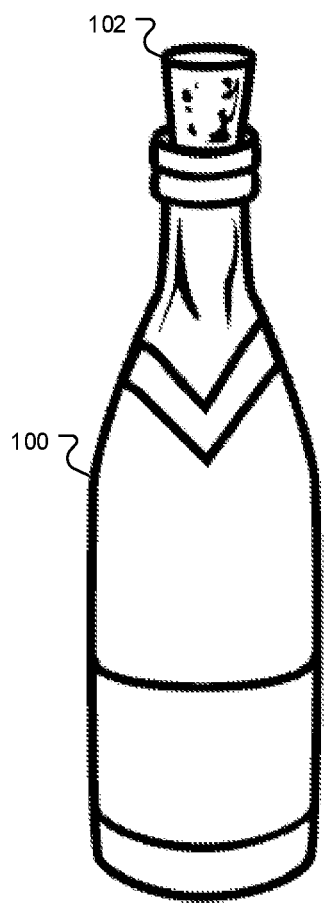
FIG. 1 illustrates a bottle of wine which may or may not be tainted.

Referring to FIG. 1, a bottle of wine 100 is illustrated that has the general size and shape of many commercially available bottles. The wine bottle 100 may be made of glass. While one particular bottle is illustrated in the figures, other bottles of similar or different size, shape and style may be utilized. Further, in some arrangements, other types of containers, vessels, etc. may be utilized, e.g., vessels for the storage or delivery of wine.

Wine faults or defects, which may be present in the wine bottle 100, can cause unpleasant olfactory and gustatory characteristics and may result from a variety of sources, such as poor hygiene at the winery, excessive and/or insufficient exposure of the wine to oxygen, excessive or insufficient exposure of the wine to sulfur, overextended maceration of the wine either pre- or post-fermentation, faulty fining, filtering and stabilization of the wine, the use of dirty oak barrels, over-extended barrel aging, the use of poor quality corks, etc. External to a winery, other factors associated with a wholesaler, retailer, end user, etc. can contribute to faults in a bottle of wine. These include poor storage and/or transport, in which the wine is e.g., exposed to excessive heat and/or temperature fluctuations.

"Cork taint" is a term used in the wine industry to describe one such wine fault, whose defining characteristics are a set of undesirable smells and tastes in a bottle of wine. In general, cork taint can be detected after the bottling and opening of a bottle of wine. Several factors can contribute to the presence of cork taint, amongst them contaminated wooden barrels, storage and transport conditions, cleaning products in a winery, contaminated machinery or bottling equipment, airborne molds etc. In some instances, a cork stopper used to seal the bottle may be responsible. It is from this process that the term "corked" has evolved to describe wine tainted in this way.

It is estimated that there are up to one thousand different molecules in wine, with most of these molecules having a similar chemical composition, and being present in very low concentrations. Some of these molecules are undesirable, such as 2,4,6-trichloroanisole (TCA) molecules, the primary cause of cork taint in a bottle of wine. Wine taint is also caused by 2,4,6-tribromoanisole (TBA) molecules, but the TBA molecule is generally less prevalent than TCA. Sulfur taint is also undesirable, and is caused by compounds like mercaptans/thiols such as ethyl mercaptan or methanethiol. The TCA molecule is typically transferred to the wine from the cork stopper, but it may also come from other sources, and introduced either by the cork or before bottling. In general, wine containing TCA has a characteristic odor, predominantly described as resembling the scent of a moldy substance. In addition to wine, TCA can also be found in bottled water, beer, spirits, soft drinks, and other food products.

Molecules of interest like TCA and methanethiol contain distinctive chemical bonds that distinguish them from the rest of the molecules in wine, and which yield characteristic spectroscopic signals (e.g., Raman frequency shifts) that are unique to these molecules. In the case of TCA, this is due to the presence of a carbon-chlorine bond, and in the case of methanethiol, this is due to the presence of a carbon-sulfur bond.

TCA may be produced as a result of the interaction between microbes and chlorinated phenolic compounds present in natural cork (more specifically, these microbes convert chlorophenols into chlorinated anisole derivatives, which are then present in the cork and dissolve into the wine), but they can also arise in the absence of microbes. The chlorophenols can be absorbed by cork trees from contaminants in pesticides and wood preservatives. Further, chlorophenols can be a product of the chlorine bleaching process used to sterilize or bleach, wood, cork, and paper, or they can migrate from other objects, such as shipping pallets that have been treated by chlorophenols. The microbes that produce TCA can be mold-forming fungi that live in small pores in the bark of cork trees, airborne fungi in the facility, and bacteria or fungi like *Aspergillus* spores, *Penicillium* spores *Actinomycetes, Botrytis cinerea, Rhizobium* spores, *Streptomyces*, etc.

Typically, corked wine is unpalatable because its natural aromas are reduced significantly. Severely corked wine can be undrinkable. Not only does this lead to unhappy customers, but it also increases transactional costs due to the corrective action required upon detecting a "corked" bottle of wine (e.g., removing the tainted bottle from the supply chain, returning the bottle to the wine retailer, etc.).

Figure 2:
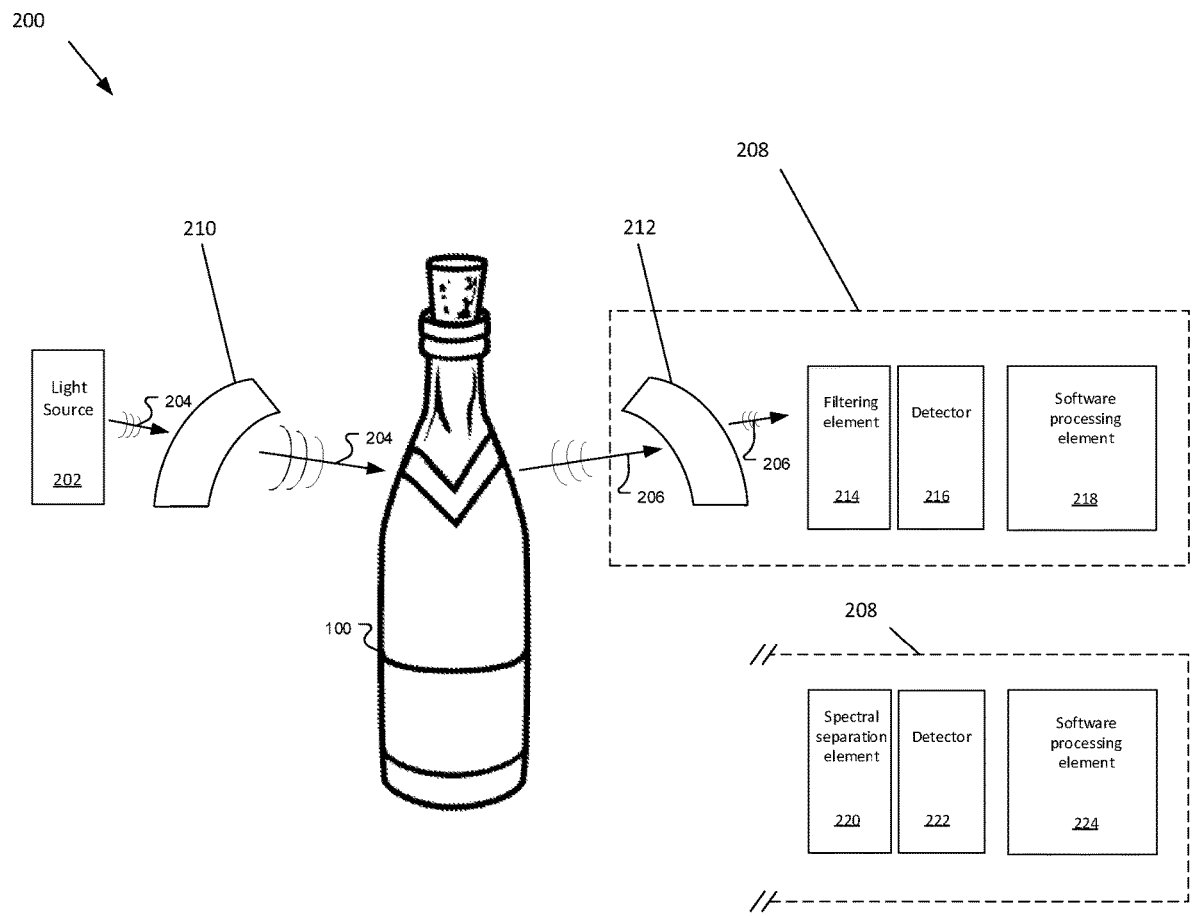
FIG. 2 illustrates a system for detecting tainted wine that is incorporated into a device.

Referring to FIG. 2, a system is illustrated that is capable of detecting tainted wine and other types of abnormalities and/or characteristics, e.g., by detecting TCA or other molecules of interest in a bottle of wine by using spectroscopy. Spectroscopy is a non-invasive technique, so, using the system, the molecules of interest can be detected prior to opening the bottle of wine. Using the system, a purchaser can determine whether a bottle should be returned or possibly not purchased in the first place, without the need to open the bottle. A producer can also keep back tainted bottles, guaranteeing production of taint-free wine, and a supplier can filter the wine they buy and resell. The system can also suppress the occurrence of embarrassing events both in restaurants and in private (e.g., serving tainted wine to friends, feeling intimidated by a sommelier etc.).

One or more techniques may be employed to detect wine taint in a non-invasive manner. For example, a spectroscopic system may be employed to detect the presence of the molecules of interest and render a determination of whether the wine is tainted or not. In this arrangement, the detection system is incorporated into a device 200, which is easily portable and either includes or can be adapted to include data collection, processing, and presentation needs. The device 200 includes a light source 202 that emits light (sometimes referred to as incident light 204) into the bottle 100. In some implementations, the light source is a laser. In some implementations, the light source is an LED. The incident light 204 may pass through an optical sampling/filtering element 210 before it is incident on the bottle 100. The incident light 204 interacts with the contents of the bottle and is scattered in an omnidirectional manner. The scattered light 206 can contain faint "optical fingerprints" of the different molecules present in the wine. The "optical fingerprints" correspond to peaks or dips where the scattered light 206 has been scattered or absorbed by particular molecules. In this way, the term "scattered light" 206 emerging from the bottle 100 may include light that is transmitted, reflected, refracted, and dispersed, and constitutes light that has been scattered or absorbed and emitted on an atomic/molecular level due to the liquid in the bottle 100.

In this arrangement, the device 200 includes a detection system 208 that is capable of collecting the scattered light 206. The detection system 208 may include an optical collection element 212 that the scattered light 206 passes through before being incident on the detection system 208. The detection system 208 can include a filtering element 214 (e.g., one or more optical filters), a detector 216 (e.g., a charge-coupled device (CCD) detector or a photodiode), and a software processing element 218 (e.g., software, hardware, or a combination of software and hardware). The information carried by the scattered light 206 is provided to the software processing element 218, which processes the collected information and determines whether the wine contained in the bottle 100 is tainted or not.

In some implementations, the scattered light 206 can go through one or more pre-processing steps before the information carried by the scattered light 206 is provided to the software processing element 218. For example, the filtering element 214 can include a bandpass filter that isolates one of the "optical fingerprints" that corresponds to a peaks or dip where the scattered light 206 has been scattered or absorbed by a particular molecule. The filtering element 214 can also include one or more other filters for filtering unwanted signals apart from the peaks or dips of the molecule of interest, such as Rayleigh scattered light, unwanted fluorescence, etc. Following filtering by the filtering element 214, the scattered light 206 is directed onto a surface of the detector 216. In such an implementation, the detector 216 can be a photodiode which to provides an output to the software processing element 218 that indicates the presence of molecules of interest such as TCA molecules in the wine contained in the bottle. The software processing element 218 can then compare the output of the detector 216 to a threshold value to determine whether a signal is present.

In some implementations, the detection system 208 includes a spectral separation element 220, a detector 222, and a software processing element 224. The scattered light 206 goes through one or more pre-processing steps before the information carried by the scattered light 206 is provided to the software processing element 224 (e.g., a different software processing element than the software processing element 218 described above). That is, the scattered light 206 is primarily processed by the software processing element 224 to remove unwanted signals apart from the peaks or dips of interest. In such an implementation, the spectral separation element 220, which can include a diffraction grating, is configured to spectrally separate the scattered light 206. Following spectral separation by the diffraction grating, the scattered light 206 is directed onto a surface of the detector 222 (e.g., a different detector than the detector 216 described above). In such an implementation, the detector 222 can be a CCD detector. The detector 222 then provides an output to the software processing element 224, which processes the output to determine whether a signal of interest is present in the scattered light 206.

One or more mechanical implementations may be designed to interface the light source 202, the optical sampling/filtering element 210, and/or the detection system 208 to the bottle 100. For example, one or more mechanical clamps and/or structures that conform to the bottle's shape may be used to appropriately position the system components such that they can interact with the bottle's 100 contents. In one arrangement, a housing structure may provide an interface between the device 200 and the bottle 100 (e.g., the housing clamps or slides over the bottle). In another arrangement, the device 200 is designed to fit around the bottle (e.g., in a "donut" configuration).

Various processing techniques may be employed by the detection system 208 in order to collect and process the information needed to determine whether the wine is tainted. For example, as described above, one or more filtering operations may be executed on the scattered light 206, on one or more signals produced from the scattered light 206 by the detection system 208, or on a combination of the scattered light 206 and the corresponding signal(s), etc. Through particular filtering operations (e.g., selecting appropriate frequency ranges), the fingerprint of the molecule of interest may be detected in the wine.

Parameters of the incident light 204 and the light source 202 may be selected based upon an interaction of the incident light 204 with the bottle 100 and its contents. In general, when the incident light 204 interacts with the molecules contained in the wine, the light may be absorbed (and later re-emitted) or the light may be scattered. The former process forms the basis of the measurement technique known as absorption spectroscopy, while the latter process forms the basis for the measurement technique known as Raman spectroscopy. Either of these techniques, or variations thereof, may be applied to the detection of molecules of interest.

For molecules, two types of scattering may occur. The first type of scattering, Rayleigh scattering, is an "elastic scattering" process in which a photon bounces off a molecule like a billiard ball, emerging with the same energy as it entered. The second type of scattering, Raman scattering, is an inelastic scattering process in which the light scattered by a molecule emerges having an energy level that is slightly different (more or less) than the incident light. This energy difference is generally dependent on the chemical structure of the molecules involved in the scattering process.

Typically, most scattering that occurs in nature is Rayleigh scattering. For example, Rayleigh scattering provides the blue color to the sky: the intensity of the light that gets Rayleigh scattered by a molecule is inversely proportional to the fourth power of the wavelength of the incident light, which means that blue light (shorter wavelength) is scattered 10 times more than red light (longer wavelength), and hence sunlight incident on gas molecules in the air gets scattered as blue light in every direction. Comparatively, Raman scattering is less prevalent. For approximately one million photons Rayleigh scattered by a molecule, only one or a few photons are Raman scattered. Therefore, the most significant challenge in Raman spectroscopy is to separate the Raman scattered light from the predominant Rayleigh scattering that accompanies it. The comparative scarcity of Raman scattering also means that it can be considered more difficult to detect than Rayleigh scattering.

Raman spectroscopy is based on the fact that different molecular vibrations within a sample translate into bigger or smaller shifts in frequency for any Raman scattered light, and because this vibrational information is specific to the chemical bonds and symmetry of the molecules, the frequency shifts translate into a specific molecular structure. Thus, Raman spectroscopy can be considered as a powerful investigative tool capable of providing "optical fingerprints" by which molecules can be identified, for example TCA, methanethiol, etc.

More technically speaking, a Raman scattering event can proceed as follows. An incoming photon interacts with a molecule and polarizes the cloud of electrons around the nuclei, exciting the molecule to a virtual energy state (i.e. not one of the molecule's real excited states, but a state created by the photon induced polarization, whose energy is determined by the frequency of the incident photon). This state is not stable and the photon is quickly re-radiated, or scattered. If nuclear motion is induced during the scattering process, energy will be transferred either from the incident photon to the molecule or from the molecule to the scattered photon. The process is inelastic, and the energy of the scattered photon will differ from that of the incident photon by one vibrational unit. Because the vibrational states of the molecule are dictated by its chemical structure, the shift in energy of the scattered photon will likewise then contain information about that chemical structure. If nuclear motion is not induced and only electron cloud distortion is involved in the process, then the photon will be scattered with only a negligible change in frequency as electrons are comparatively light, this (nearly) elastic scattering process is Rayleigh scattering.

Different molecules are made up of different atoms in different configurations, so each molecule bends, stretches, and vibrates in a slightly different way. Some of the photons scattered by a molecule will change the way the molecule is vibrating, and in turn, the energy of those photons will be changed by a very small amount. This change in energy is directly proportional to the vibration of the molecule, and hence to its chemical configuration, so Raman scattered light can be thought of as an "optical fingerprint" that can be used to identify a molecule by its chemical structure. Other spectroscopic techniques may be used to investigate molecules, and could be used to detect molecules of interest with practically the same components as necessary for Raman spectroscopy.

One example is the technique of absorption spectroscopy. Absorption of light by molecules occurs at frequencies that are dictated by their chemical structure. More specifically, absorption occurs at wavelengths that match one of the electronic, rotational, or vibrational transitions of a molecule. Hence a dip in transmission at a given wavelength indicates the presence of a molecular transition at that wavelength. Because electronic, rotational, and vibrational transitions are particular to the chemical structure and symmetry of a molecule, the various dips in transmission recorded can be used to determine the presence of a given molecule. The dips in transmission observed in absorption spectroscopy are analogous to the shifts in frequency observed in Raman spectroscopy, and they too can be seen as "optical fingerprints" by which molecules can be identified (in fact the absorption spectrum and the Raman spectrum of a given molecule often resemble each other quite closely).

One key difference between the two techniques is that in absorption spectroscopy, the illuminating laser has to be tuned to excite the transition frequencies of the bonds or groups that vibrate for the molecule in question, whereas in Raman spectroscopy, the illuminating laser can be tuned to an arbitrary virtual energy state. Another example of a technique that can be used to investigate molecules is laser induced breakdown spectroscopy. In this technique, a pulsed laser is focused to a small spot within a sample. This highly energetic laser pulse forms a plasma in its focus, atomizing the molecules therein. As the plasma cools, excited atoms in the plasma emit light of characteristic wavelengths distinctive to the plasma. This light contains the "optical fingerprint" of the elements contained in the molecules ablated by the laser pulse, and can therefore also be used to investigate their chemical structure.

In implementations in which Raman spectroscopy is employed, a spectrometer can include a light source, a sampling apparatus, and a detector. In the illustrated example, equivalent functionality is provided by the light source 202, the optical sampling/filtering element 210, and the detection system 208, individually or in concert (based upon the design). From a functional perspective, the light source 202 (e.g., a laser or an LED source) provides incident light for the molecules to scatter, and the detection system 208 collects, spectrally separates and/or filters the scattered light and measures the signal. While this functionality may be common to numerous Raman spectrometers, the design of the individual components (e.g., light source, detection system) may vary based upon system and component parameters (e.g., operating wavelength, detector sensitivity, spectrograph used to separate the scattered light, physical footprint, etc.).

One or more system and component parameters, features, etc. may be defined for spectroscopic analysis and detection of molecules present in the wine bottle 100. For example, a relatively long wavelength may be chosen for the light source 202 such that the tinted glass (e.g., of the wine bottle 100) and the pigments in the wine are practically "invisible" to the incident light. In one arrangement, a 1064 nm laser may be employed to perform Raman spectroscopy. Lasers of this type are generally considered advantageous for Raman spectroscopy because they allow for substantial suppression of unwanted background absorption and fluorescence (absorbed and re-emitted light from molecules other than the molecules of interest) that can accompany and overwhelm the desired Raman scattered light. In the particular application of TCA detection in bottles of wine, most of the unwanted background absorption and fluorescence can come from the tinted glass bottle and the pigments in the wine. The laser used can be a continuous or pulsed laser, for example an NdYag (neodymium-doped yttrium aluminum garnet) laser.

In one implementation, the light source 202 can be a continuous-wave diode-pumped solid-state laser with a wavelength of 1064 nm and a maximal output power of 3.5 watts, a 05-01 Series Rumba™ laser from Cobolt AB. The power of the laser is chosen so as to maximize the signal obtained from the desired molecule in the bottle of wine. The strength of the signal from a particular molecule is proportional to its concentration in the wine as well as to the power of the laser exciting the Raman transition that gives rise to this signal. Hence, a laser with a higher power leads to a stronger signal (if there are more photons impinging on the molecule per unit time, there will be more Raman scattered photons detected per unit time, and hence a stronger signal). For detecting wine taint, various types of detectors may be employed. For example, a germanium photodiode detector that is sensitive in the spectral fingerprint region of organic molecules like TCA may be used in the detection system 208. This fingerprint region can be considered to reside in the near-infrared (NIR) mid-infrared (MIR) frequency range, with the Raman frequency shifts located between 400 and 4000 $cm^{-1}$ (inverse centimeter unit, often used for spectroscopy) corresponding to wavelengths of 2.5 to 25 µm. This fingerprint region can also be considered as including Raman scattered light with a wavelength range (rather than shift) of e.g., 1.11 to 1.85 µm. For example, the detector 216 or 222 can be a germanium photodiode sensitive in the near infrared region between 700 and 1800 nm from Thorlabs GmbH. Its power range is from 5 nW to 500 mW, and it has a resolution of 1 nW. This wide range in sensitivities allows the photodiode both to detect the Raman scattered light and to align the optical components in the device. The photodiode is read out by the PM100USB console, also from Thorlabs. This console allows computer control of the attached sensor and can be used with several different detectors.

In some implementations, the photodiode can be replaced by two photodiodes, one which is sensitive at powers below 1 nW and has a higher resolution, to be used for detection, and a second one which is sensitive at powers up to 3 W, to be used for alignment.

In some implementations, the detector can be TE-cooled indium gallium arsenide (InGaAs) detector.

Along with different detector types, detection parameters may be defined and adjusted for the application. For example, to provide the requisite level of sensitivity, an appropriate signal-to-noise ratio may be needed and provided through one or more procedures, such as the suppression of unwanted light (e.g., stray light from the light source 202, noisy ambient light, Rayleigh scattered light, background fluorescence, etc.). Following suppression of unwanted light and spectral separation by a spectrograph, the obtained signal will consist of the total Raman spectrum of all the molecules contained in the bottle of wine. Further techniques may be employed in order to isolate and distinguish the Raman signal of a molecule of interest from the Raman signal of other molecules contained in this spectrum. In one arrangement, the Raman spectra of unwanted molecules within the total spectrum may be identified by previous knowledge of these spectra (e.g., by previous tabulation, measurement, etc.) after spectral separation by a spectrograph and removed (e.g., by vector subtraction). The previous knowledge requisite can be incorporated into the software processing operations of the software processing element 224 of the detection system 208.

As described above, in another arrangement, optical filters remove all but part of the desired Raman spectrum from the total obtained signal before it is detected, without the need for spectral separation. In this arrangement, it may be possible to use a photodiode as the detector 216 instead of a CCD. The spectra of unwanted reflections from the wine bottle (e.g., at the air/bottle interface, the bottle/wine interface, etc.) can also be characterized (e.g., estimated, measured, etc.) and included in one or more pre-processing and/or processing operations (e.g., before information carried by the scattered light 206 is provided to the software processing element 218). Such pre-processing and/or processing operations can include removal of the unwanted spectra.

To identify the desired spectrum for the molecule of interest, one or more techniques can be employed, e.g., optical and/or signal filtering, amplifying, etc. To manipulate the incident light 204 and the scattered light 206 preceding the acquisition of this spectrum, different design parameters may be employed. In one arrangement, the scattered light 206 scattered by the contents of the bottle may be collected along the same path as the incident light (e.g., in the backwards direction in a monostatic manner) by means of a dichroic mirror that is capable of separating the scattered light 206 from the incident light 204 and redirecting the scattered light 206 along a different path than the incident light 204. In another arrangement, the scattered light may be collected on the same axis as the incident light 204, but on the other side of the bottle 100 (i.e., in the forward direction in a bistatic manner). In another arrangement, the scattered light 206 may be collected in the forward direction, the backward direction, and at a range of angles in between. Such an arrangement can maximize the strength of the collected signal, because molecules scatter light over a solid angle of 4n. Such an arrangement can be accomplished by using multiple detectors 216, 222 positioned at various points along the perimeter of the bottle 100.

In the illustrated example, light producing hardware (e.g. the light source 202 and the optical sampling/filtering element 210) and light collecting hardware (e.g., the detection system 208) are incorporated into a single device. However, one or more other types of devices, platforms, etc. may be utilized to provide the molecule of interest detection functionality.

In one arrangement, a Raman spectrometer may be used for making such measurements. Generally, such a spectrometer includes the light source 202 such as a laser or LED source, the optical sampling/filtering element 210, and the detection system 208. One or more types of lasers or LED may be used operable at a wavelength in the infrared spectral region (e.g., at approximately 1064 nanometers (nm), 940 nm, 1120 nm, 1320 nm, 1440 nm, etc.)). By operating in this spectral region, unwanted absorption and fluorescence from the wine bottle and the pigments of the contained wine can be substantially suppressed. Operating power may range from less than 500 milliwatts (mW) to more than one watt (e.g., a few watts). In general, the strength of the signal scattered by a particular type of molecule is proportional to its concentration as well as to the laser power exciting the Raman transition that produces the signal. In other words, if more photons are impinging upon the molecule per unit time, more Raman scattered photons will generally be detected per unit time, thereby producing a relatively larger signal. In some arrangements, light source parameters may be defined to minimize health and safety concerns. For example, the light source and associated optics may be placed in protective housing to reduce or prevent the probability of harming a user's eyes. In some implementations the power of the light source may be set to operate at a level that reduces the probability of harming a user's eyes (e.g., by reducing the intensity of any specular reflections.

The detection system 208 may include one or more optical collection elements 212, one or more filtering elements 214 and/or spectral separation elements 220 (e.g., one or more optical filters such as a bandpass filter or a dichroic filter, a diffraction grating such as a volume phase holographic transmission grating, etc.), various other optical components such as optical fibers, lenses, and mirrors, one or more detectors 216, 222 (e.g., one or more charge-coupled device (CCD) detectors, photodiodes, etc.), and one or more software processing elements 218, 224. Normally, the type of spectrograph used in dispersive Raman spectroscopy is a surface-relief reflective diffraction grating. Absorption spectroscopy uses a modified spectrograph of this type called a monochromator. A diffraction grating can be considered as an optical component with a periodic structure that splits and diffracts light into beams of different wavelengths. Such a periodic structure can for instance be a repeating pattern of relatively small grooves or ridges etched onto a surface at regularly spaced intervals. Diffraction gratings can be either transmissive or reflective and can modulate the phase rather than the amplitude of the incident light 204. An alternative to groove-based surface-relief diffraction gratings are volume phase holographic transmission gratings (VPHTGs). VPHGTs do not have physical grooves; instead, they contain an optically thick but transmissive dichroic gelatin film which has a periodic hardness and is positioned between layers (e.g., two) of clear glass or pure silica. The periodic hardness of the gelatin translates into a periodic refractive index which then modulates the light in a manner similar to a surface-relief pattern. VPHTGs are generally more efficient and produce less unwanted scattering.

Along with the various types of detectors that may be employed, various electronic components and other associated modules may be included with the detector to provide additional functionality. For example, data from the detector is typically read and interpreted by the software processing element 218, 224 (e.g., processed by software, hardware, or a combination of software and hardware associated with a computing device). The software processing element 218, 224 may have other functions. For example, one or more user interfaces may be provided for operational control, data acquisition, data presentation, etc.

In implementations in which the scattered light 206 is filtered by the filtering element 214 (e.g., a bandpass filter) and directed onto the surface of the detector 216 (e.g., a photodiode), the software processing element 218 compares an output of the detector 216 to a threshold value to determine whether a signal for a molecule of interest is present.

In implementations in which a Raman spectrometer is used, the scattered light 206 is spectrally separated by the spectral separation element 220 (e.g., a diffraction grating) and directed onto the surface of the detector 222 (e.g., a CCD detector), the software processing element 224 processes the signal from the scattered light 206 to remove unwanted signals apart from the signals for the molecules of interest. The Raman spectrometer generally includes a laser as the light source 202.

Depending on the implementation, various components may be used as the light source 202. For example, several high powered LEDs in the requisite near infrared region can be used.

The spectral width of such LEDs is not as narrow as that of a laser, but an additional filter may be used to narrow the spectral width. Various devices may also be used as the detector 216, 222 in the detection system 208. For example, one or more types of photodiode (e.g., avalanche photodiodes) may be used to detect the scattered light.

Different light collection techniques may be used by the detector 216. For example, the detector 216 may employ one of several filtering techniques (e.g., bandpass filters, dichroic filters, etc.) to isolate particular spectral regions (e.g., frequencies, frequency bands, etc.) having particular spectral widths. In one arrangement, a narrow bandpass filter may be used to isolate one or more of the frequency peaks associated with the signal of a molecule of interest. By focusing upon single frequencies (and not broader spectra), a single signal characteristic such as amplitude may be used to ascertain the presence of the molecule of interest (e.g., by applying one or more predetermined thresholds). In this way, the presence or absence of the molecule of interest may be determined without the need to detect, spectrally separate, and characterize the total spectrum obtained from the bottle of wine (the combined spectrum of all the molecules present within it). In such an arrangement, a spectral separation element 220 such as a spectrograph is not needed, and previous knowledge of the spectra of unwanted molecules does not need to be included in the software processing element 218.

In some implementations filtering element 214 includes two or three different filters (e.g., optical filter). The first filter may be a bandpass filter that is used to eliminate spectral noise from the incident light by blocking the transmission of substantially all but a narrow band of frequencies around a central frequency of interest which is wholly transmitted. This first filter narrows the light and eliminates unwanted frequencies (e.g., the carrier frequency). In implementations where the light source 202 is an LED (e.g., a diffuse light source) this first filter can be used, and in implementations where light source 202 is a laser with a narrow spectral linewidth this first filter can be omitted.

A second filter (e.g., optical filter) that is part of filtering element 214 can be a longpass edge filter, a notch filter, etc., and is used to suppress the unwanted Rayleigh scattered light that accompanies the Raman scattered light of interest. Longpass edge filters work by blocking transmission below a given frequency, and allowing transmission above it. Notch filters work by allowing the transmission of all but a very narrow band of frequencies around a central frequency that is wholly suppressed.

The third filter (e.g., optical filter) that is part of filtering element 214 can be a very narrow bandpass filter used to isolate the Raman scattered light of interest (e.g., for TCA, methanethiol, etc.) from the rest of the light scattered by the sample. This filter is picked such that its central wavelength matches the frequency of the Raman scattered light of interest. To isolate Raman scattered light from the molecule of interest the filter can be selected to isolate both the wavelength of particular molecule of interest as well as which of the given molecule's Raman shifts are isolated. It is also possible to do a multi-component analysis where select Raman peaks of several molecules could be isolated. To change which molecule of interest (or particular Raman shift for a molecule of interest) device 100 is detecting, the third filter used can be quickly and easily substituted for a different third filter having a different filtering capability specific to the new application.

These filters are easily interchangeable thin film disks about an inch in diameter which are available off the shelf in a variety of central wavelengths but which can also be custom made to fit a desired wavelength. As am example, the filters which make up filtering element 214 can be made by Thorlabs GmbH.

One application of multi-component analysis is to identify counterfeit bottles of wine by looking for elevated levels of certain molecules like phenolic compounds, acids, ethanol, etc., which could mean they were added and not inherent in the grapes, which is not permitted in certain regions where fine wine is made.

One or more techniques may be employed to investigate specific frequencies, relatively narrow frequency bands, etc.

The functional steps or detecting wine taint can be generally grouped into four main parts: illumination, optical processing, detection, and software processing. More specifically, a complete measurement includes initiating illumination, expanding and/or directing the illuminating light into the bottle using optical components, filtering the scattered light or signals, detecting the filtered light, processing the detected signal by software which consists of recording the power incident on the photodiode and determining whether it is above a predetermined threshold level. Finally, the result can be displayed on a graphical user interface (GUI). In some implementations, the software not only controls device 200 function and initiates measurement, but also enables storage and transmission of the obtained data.

The method described above is similar to those used in Raman spectrometers, but with differences in the filtering and signal processing. In a traditional Raman spectrometer the scattered light is optically filtered to remove the unwanted Rayleigh scattered light that accompanies the Raman scattered light of interest, and the incident light can be optically filtered to eliminate spectral noise that is not at the wavelength of interest. This is also done in device 200. However, in a Raman spectrometer, the key step in a measurement is the spectral separation of the scattered light into all of its constituent frequencies. The resulting spectrum contains the "optical fingerprints" of all the different molecules contained in the sample, is analyzed by software, and molecules are identified by comparison with a database of known molecular spectra. These two key steps in a Raman spectrometer—spectral separation and analysis by software—are sidestepped completely in device 200. In device 200, the scattered light is instead optically filtered a second time to remove all but the light at one particular frequency. This key step in device 200 does not take place in a conventional Raman spectrometer, and allows the software processing to be reduced to a simple threshold measurement. Device 200 is simplified both in terms of hardware and software.

Raman spectrometers typically extract a full spectrum for analysis to determine the composition of a sample or to identify one of several substances in a sample. However, device 200 is configured to determine a small number of predetermined molecules of interest in a sample, (e.g., TCA and methanethiol) it is not necessary to spectrally separate the scattered light and analyze the total spectrum obtained. It suffices to look for the presence of scattered light with a frequency corresponding to one of the Raman frequency shifts of the molecule of interest.

If the molecule of interest is present in the sample, Raman scattered light will have experienced the various frequency shifts associated with the molecule's different vibrational states unique to its chemical structure, allowing the assumption that the molecule of interest is present in the sample. Optimally, a frequency shift is chosen which is particular to the molecule of interest and does not coincide with any of the Raman shifts of other molecules that may be found in the sample.

By optically filtering the scattered light and focusing upon a single frequency, it is possible to just use the amplitude of the measured signal and a predetermined threshold value to ascertain the presence or absence of a given molecule, without the need to obtain or characterize the total combined Raman spectrum of all the molecules present in the sample using software. If light falls on the detector 216 and the amplitude of the signal recorded is above the threshold value, then the molecule of interest is present in the sample; if no light falls on the detector 216 or the signal is below the threshold value, then the molecule is not present in the sample at a detectable level.

This threshold determination at a single frequency means that software processing is reduced to a simple yes/no determination. Furthermore, the CCD detector used in typical Raman spectrometers is replaced by a photodiode. The molecule of interest detected can be changed by changing the value of frequency that is optically filtered from the scattered light, requiring the substitution of one small component.

The same technique could apply to a device based on infrared absorption spectroscopy instead of Raman spectroscopy. Infrared absorption spectroscopy requires that infrared light covering a range of wavelengths be directed onto the sample. The wavelength range of interest is either scanned by using a monochromator, or the scanning is simulated by means of a technique called infrared Fourier Transform spectroscopy, which allows for all frequencies to be collected simultaneously in a large range. In this implementation, if there is only one predetermined molecule of interest in a sample, it would not be necessary to extract the full absorption spectrum of the sample. Rather, device 200 detects the absence of scattered light at a frequency corresponding to one of the dips in transmission associated with the molecule's different vibrational states. Thus, a device based on infrared absorption would be functionally similar to the one based on Raman scattering.

For example, using one technique, a filter or a combination of filters may be used to focus on the TCA, methanethiol, etc. response of the received signal. Various types of filtering techniques could be incorporated into the filtering element 214 of the detection system 208. For example, bandpass filters, notch filters, edge filters (long pass or short pass filters), etc. may be used to help isolate the response of the molecule of interest. Such filters may serve several purposes conducive to the isolation of the signal, e.g., narrowing the frequency of the incoming light, suppressing Rayleigh scattering, isolating a peak in the molecule of interest spectrum, etc. To suppress unwanted light signals, various types of processing techniques can be used. For example, calibration techniques may be used to first characterize signal sources other than molecule of interest (e.g., unwanted Raman scattering or fluorescence from the bottle, water molecules, etc.). Once characterized (e.g., within the frequency bands of interest), one or more processing techniques may be employed to substantially suppress, remove, etc. signal content associated with these unwanted sources. For example, estimation techniques, measurements, etc. may be used to determine the spectrum of the unwanted signal sources within the frequency bands of interest. Next, these determined spectral quantities represented by, e.g., amplitude, may be removed from the total signal response of the wine present in the bottle 100, leaving only the spectral response of the molecule of interest. In a sense, the data representing light signals (e.g., scattering or fluorescence) from unwanted sources can be removed enough to substantially isolate the signal gathered from the molecule of interest. Once isolated, the signal can be processed (e.g., by the software processing element 218, 224) to determine if the wine should be considered "corked" or appropriate for consumption.

Once this information is collected, processed, etc., additional operations and functionality may be employed. For example, one or more networking techniques (e.g., wireless networking) may be used to distribute the obtained data to other relevant persons (e.g., wine producers, distributors, etc.), facilities (e.g., storage sites, processing locations, etc.), etc. for dissemination and later use. The data may also be provided to facilities for storage, further analysis and presentation (e.g., on a web-based asset such as a website). The data may be used for a variety of applications, such as comparative studies, on-going wine storage transportation analysis, etc.

Figure 3:
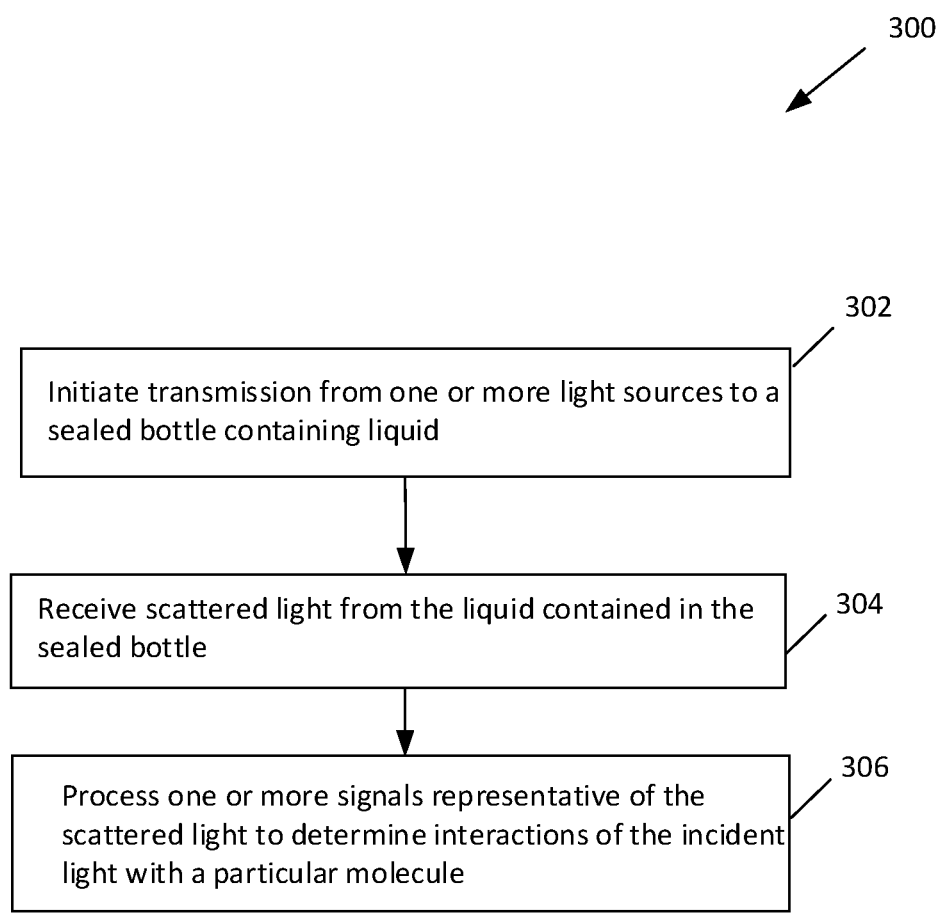
FIG. 3 is an example flow chart of operations for detecting tainted wine.

Referring to FIG. 3, a flowchart 300 illustrates the operations of the liquid fault detection system (e.g., the light source 202, the optical sampling/filtering element 210 and the detection system 208 shown in FIG. 2). Operations of the fault detection system are typically executed by a single device (e.g., the device 200). However, operations may also be executed by multiple devices. Along with being executed at a single site (e.g., the location of a wine bottle), the execution of operations may be distributed among two or more locations. In some arrangements, a portion of the operations may be executed at a central location (e.g., a wine data center or similar facility).

Operations of the liquid fault detection system may include initiating 302 transmissions of incident light from one or more light sources to a sealed bottle containing liquid. For example, a wine bottle (e.g. the wine bottle 100) may be illuminated as initiated by a light source incorporated into a device (e.g., a laser, LED, etc. provided by the light source 202 of the device 200). Operations also include receiving 304 scattered light from the liquid contained in the sealed bottle. For example, scattered light from the bottle and the liquid content of the bottle may be received by a detector incorporated into the device (e.g., the detector 216, 222 of the detection system 208). Operations can also include processing 306 one or more signals representative of the scattered light to detect interactions of the incident light with a particular molecule present in the contained liquid. For example, the particular molecule may be TCA. The scattered light may be filtered prior to processing one or more signals representative of the scattered light. The scattered light may also be filtered prior to being received (e.g., by a detector such as the filtering element 214, which can be a bandpass filter that isolates one of the peaks in the TCA frequency spectrum). The scattered light may also be filtered as part of the processing. In this way, processing one or more signals representative of the scattered light includes filtering the signals. Alternatively, the scattered light may be spectrally separated (e.g., by the spectral separation element 220) prior to processing one or more signals representative of the scattered light, and the scattered light may be filtered subsequent to being received by a detector (e.g., by subtracting unwanted signals from the total obtained spectrum with the software processing element 218, 224). By blocking or subtracting unwanted light signals in this way, a representative measure of the amount of TCA present in the contained wine may be produced.

Figure 4:
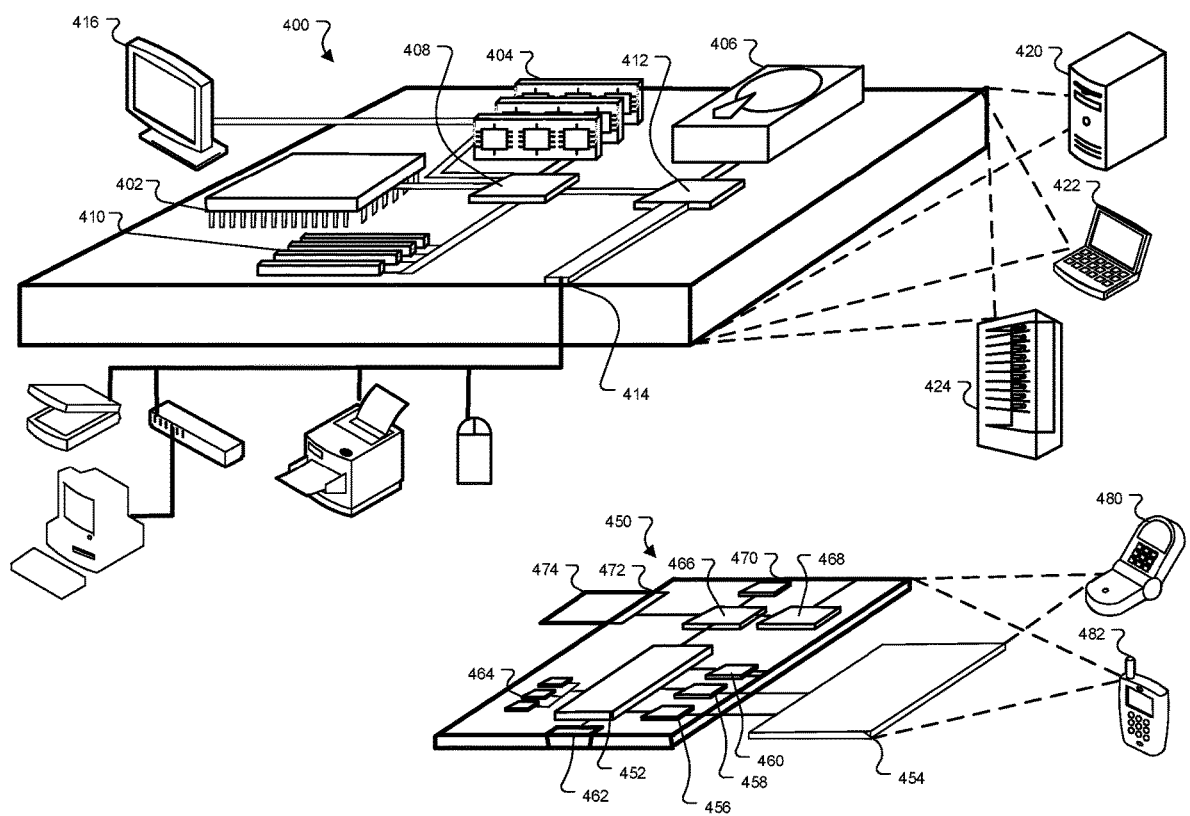
FIG. 4 illustrates an example of a computing device and a mobile computing device that can be used to implement the techniques described here.

FIG. 4 shows an example computer device 400 and an example mobile computer device 450 (e.g., which can be, e.g., the device 200), which can be used to implement the techniques described herein. For example, a portion or all of the operations of the light source 202, the optical sampling/filtering element 210, and the detection system 208 (shown in FIG. 2) may be executed by the computer device 400 and/or the mobile computer device 450. Computing device 400 is intended to represent various forms of digital computers, including, e.g., laptops, desktops, workstations, personal digital assistants, servers, blade servers, mainframes, and other appropriate computers. Computing device 450 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 400 includes processor 402, memory 404, storage device 406, high-speed interface 408 connecting to memory 404 and high-speed expansion ports 410, and low speed interface 412 connecting to low speed bus 414 and storage device 406. Each of components 402, 404, 406, 408, 410, and 412, are interconnected using various busses, and can be mounted on a common motherboard or in other manners as appropriate. Processor 402 can process instructions for execution within computing device 400, including instructions stored in memory 404 or on storage device 406 to display graphical data for a GUI on an external input/output device, including, e.g., display 416 coupled to high speed interface 408. In other implementations, multiple processors and/or multiple busses can be used, as appropriate, along with multiple memories and types of memory. Also, multiple computing devices 400 can be connected, with each device providing portions of the necessary operations (e.g., as a server bank, a group of blade servers, or a multi-processor system).

Memory 404 stores data within computing device 400. In one implementation, memory 404 is a volatile memory unit or units. In another implementation, memory 404 is a non-volatile memory unit or units. Memory 404 also can be another form of computer-readable medium (e.g., a magnetic or optical disk. Memory 404 may be non-transitory.)

Storage device 406 is capable of providing mass storage for computing device 400. In one implementation, storage device 406 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above). The data carrier is a computer- or machine-readable medium, (e.g., memory 404, storage device 406, memory on processor 402, and the like).

High-speed controller 408 manages bandwidth-intensive operations for computing device 400, while low speed controller 412 manages lower bandwidth-intensive operations. Such allocation of functions is an example only. In one implementation, high-speed controller 408 is coupled to memory 404, display 416 (e.g., through a graphics processor or accelerator), and to high-speed expansion ports 410, which can accept various expansion cards (not shown). In the implementation, low-speed controller 412 is coupled to storage device 406 and low-speed expansion port 414. The low-speed expansion port, which can include various communication ports (e.g., USB, Bluetooth®, Ethernet, wireless Ethernet), can be coupled to one or more input/output devices (e.g., a keyboard, a pointing device, a scanner, or a networking device including a switch or router, e.g., through a network adapter.)

Computing device 400 can be implemented in a number of different forms, as shown in FIG. 4. For example, it can be implemented as standard server 420, or multiple times in a group of such servers. It also can be implemented as part of rack server system 424. In addition or as an alternative, it can be implemented in a personal computer (e.g., laptop computer 422). In some examples, components from computing device 400 can be combined with other components in a mobile device (not shown), e.g., device 450. Each of such devices can contain one or more of computing device 400, 450, and an entire system can be made up of multiple computing devices 400, 450 communicating with each other.

Computing device 450 includes processor 452, memory 464, an input/output device (e.g., display 454, communication interface 466, and transceiver 468), among other components. Device 450 also can be provided with a storage device, (e.g., a microdrive or other device) to provide additional storage. Each of components 450, 452, 464, 454, 466, and 468, are interconnected using various buses, and several of the components can be mounted on a common motherboard or in other manners as appropriate.

Processor 452 can execute instructions within computing device 450, including instructions stored in memory 464. The processor can be implemented as a chipset of chips that include separate and multiple analog and digital processors. The processor can provide, e.g., for coordination of the other components of device 450 (e.g., control of user interfaces, applications run by device 450, and wireless communication by device 450).

Processor 452 can communicate with a user through control interface 458 and display interface 456 coupled to display 454. Display 454 can be, e.g., a TFT LCD (Thin-Film-Transistor Liquid Crystal Display) or an OLED (Organic Light Emitting Diode) display, or other appropriate display technology. Display interface 456 can include appropriate circuitry for driving display 454 to present graphical and other data to a user. Control interface 458 can receive commands from a user and convert them for submission to processor 452. In addition, external interface 462 can communicate with processor 452 so as to enable near area communication of device 450 with other devices. External interface 462 can provide, e.g., for wired communication in some implementations, or for wireless communication in other implementations, and multiple interfaces also can be used.

Memory 464 stores data within computing device 450. Memory 464 can be implemented as one or more of a computer-readable medium or media, a volatile memory unit or units, or a non-volatile memory unit or units. Expansion memory 474 also can be provided and connected to device 450 through expansion interface 472, which can include, e.g., a SIMM (Single In Line Memory Module) card interface. Such expansion memory 474 can provide extra storage space for device 450, or also can store applications or other data for device 450. Specifically, expansion memory 474 can include instructions to carry out or supplement the processes described above, and can include secure data also.

Thus, e.g., expansion memory 474 can be provided as a security module for device 450, and can be programmed with instructions that permit secure use of device 450. In addition, secure applications can be provided through the SIMM cards, along with additional data, (e.g., placing identifying data on the SIMM card in a non-hackable manner.) The memory can include, e.g., flash memory and/or NVRAM memory, as discussed below. In one implementation, a computer program product is tangibly embodied in a data carrier. The computer program product contains instructions that, when executed, perform one or more methods (e.g., those described above). The data carrier is a computer- or machine-readable medium (e.g., memory 464, expansion memory 474, and/or memory on processor 452), which can be received, e.g., over transceiver 468 or external interface 462.

Device 450 can communicate wirelessly through communication interface 466, which can include digital signal processing circuitry where necessary. Communication interface 466 can provide for communications under various modes or protocols (e.g., GSM voice calls, SMS, EMS, or MMS messaging, CDMA, TDMA, PDC, WCDMA, CDMA2000, or GPRS, among others.) Such communication can occur, e.g., through radio-frequency transceiver 468. In addition, short-range communication can occur, e.g., using a Bluetooth®, WiFi, or other such transceiver (not shown). In addition, GPS (Global Positioning System) receiver module 470 can provide additional navigation- and location-related wireless data to device 450, which can be used as appropriate by applications running on device 450. Sensors and modules such as cameras, microphones, compasses, accelerators (for orientation sensing), etc. may be included in the device.

Device 450 also can communicate audibly using audio codec 460, which can receive spoken data from a user and convert it to usable digital data. Audio codec 460 can likewise generate audible sound for a user, (e.g., through a speaker in a handset of device 450.) Such sound can include sound from voice telephone calls, recorded sound (e.g., voice messages, music files, and the like) and also sound generated by applications operating on device 450.

Computing device 450 can be implemented in a number of different forms, as shown in the figure. For example, it can be implemented as cellular telephone 480. It also can be implemented as part of smartphone 482, a personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; e.g., feedback provided to the user can be a form of sensory feedback; e.g., visual feedback, auditory feedback, or tactile feedback; and input from the user can be received in a form, including acoustic, speech, or tactile input.

The systems and techniques described here can be implemented in a computing system that includes a backend component (e.g., as a data server), or that includes a middleware component (e.g., an application server), or a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

While the system has been described as being capable of detected tainted wine by detecting TCA or methanetiol, the system can alternatively be used to detect the presence of other molecules in other liquids. For example, the system can be used to detect the presence of lactic, malic, and/or citric acid molecules in a liquid (e.g., a wine). In another example, the system can be used to detect the presence of harmful bacteria in a medical fluid (e.g., an IV drip).

While the system has been described as employing Raman spectroscopy, other types of spectroscopy can be employed. For example, the system of FIG. 2 may employ absorption spectroscopy or laser induced breakdown spectroscopy. The various components of the system may be configured to be operational with the alternative type of spectroscopy.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A computing device implemented method comprising:
initiating transmission of incident light from one or more light sources to a sealed bottle containing liquid;
receiving scattered light from the sealed bottle and the liquid contained in the sealed bottle;
separating the scattered light from the liquid from the scattered light from the sealed bottle; and
processing one or more signals representative of the scattered light from the liquid to detect interactions of the incident light with a particular molecule.

2. The computing device implemented method of claim 1, further comprising: filtering the scattered light prior to processing one or more signals representative of the scattered light.

3. The computing device implemented method of claim 1, wherein processing one or more signals representative of the scattered light comprises filtering signals.

4. The computing device implemented method of claim 3, wherein filtering the scattered light comprises passing frequencies of the received scattered light that are within a particular frequency range.

5. The computing device implemented method of claim 1, further comprising: spectrally separating the scattered light prior to processing one or more signals representative of the scattered light.

6. The computing device implemented method of claim 1, wherein the liquid is wine.

7. The computing device implemented method of claim 1, wherein the particular molecule is trichloroanisole or methanethiol.

8. The computing device implemented method of claim 7, wherein processing comprises determining from the interactions of the incident light with the trichloroanisole molecule or methanethiol if the liquid is tainted.

9. The computing device implemented method of claim 1, wherein processing one or more signals representative of the scattered light comprises determining if the received scattered light is above a threshold value.

10. The computing device implemented method of claim 1, wherein the light source comprises a laser.

11. A system comprising:
a computing device comprising:
a memory configured to store instructions; and
a processor to execute the instructions to perform operations comprising:
initiating transmission of incident light from one or more light sources to a sealed bottle containing liquid;
receiving scattered light from the sealed bottle and the liquid contained in the sealed bottle;
separating the scattered light from the liquid from the scattered light from the sealed bottle; and
processing one or more signals representative of the scattered light from the liquid to detect interactions of the incident light with a particular molecule.

12. The system of claim 11, wherein the liquid is wine.

13. The system of claim 11, wherein the particular molecule is trichloroanisole.

14. The system of claim 13, wherein processing comprises determining from the interactions of the incident light with the trichloroanisole molecule if the liquid is tainted.

15. The system of claim 11, wherein the light source comprises a laser.

16. One or more non-transitory computer-readable media storing instructions that are executable by a processing device, and upon such execution cause the processing device to perform operations comprising:
initiating transmission of incident light from one or more light sources to a sealed bottle containing liquid;
receiving scattered light from the sealed bottle and the liquid contained in the sealed bottle;
separating the scattered light from the liquid from the scattered light from the sealed bottle; and
processing one or more signals representative of the scattered light from the liquid to detect interactions of the incident light with a particular molecule.

17. The non-transitory computer-readable media of claim 16, wherein liquid is wine.

18. The non-transitory computer-readable media of claim 16, wherein the particular molecule is trichloroanisole.

19. The non-transitory computer-readable media of claim 18, wherein processing comprises determining from the interactions of the incident light with the trichloroanisole molecule if the liquid is tainted.

20. The non-transitory computer-readable media of claim 16, wherein the light source comprises a laser.

* * * * *